(12) United States Patent
Raad et al.

(10) Patent No.: US 7,713,472 B2
(45) Date of Patent: May 11, 2010

(54) ANTISEPTIC DERIVATIVES WITH BROAD SPECTRUM ANTIMICROBIAL ACTIVITY FOR THE IMPREGNATION OF SURFACES

(75) Inventors: Issam Raad, Houston, TX (US); Hend A. Hanna, Houston, TX (US); Nabeel Nabulsi, Katy, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1086 days.

(21) Appl. No.: 10/044,842

(22) Filed: Jan. 11, 2002

(65) Prior Publication Data
US 2003/0078242 A1  Apr. 24, 2003

Related U.S. Application Data

(60) Provisional application No. 60/261,447, filed on Jan. 12, 2001, provisional application No. 60/316,165, filed on Aug. 30, 2001.

(51) Int. Cl.
A61L 2/16 (2006.01)
(52) U.S. Cl. ........................................ 422/28; 514/642
(58) Field of Classification Search ................... 422/28; 514/642
See application file for complete search history.

(56) References Cited

U.S. PATENT DOCUMENTS

| | | | | |
|---|---|---|---|---|
| 2,449,274 A * | 9/1948 | Broll | ................. | 424/10.3 |
| 3,635,652 A | 1/1972 | Streck | ................. | 8/4 |
| 4,015,937 A | 4/1977 | Miyamoto et al. | ........... | 23/230 |
| 4,107,121 A | 8/1978 | Stoy | ................. | 260/29.6 |
| 4,204,978 A * | 5/1980 | Ibsen et al. | ........... | 433/217.1 |
| 4,442,133 A | 4/1984 | Greco et al. | ................. | 427/2 |
| 4,895,566 A | 1/1990 | Lee | ................. | 604/265 |
| 4,917,686 A | 4/1990 | Bayston et al. | ........... | 604/265 |
| 4,952,419 A | 8/1990 | De Leon et al. | ........... | 427/2 |
| 5,013,306 A | 5/1991 | Solomon et al. | ........... | 604/265 |
| 5,120,325 A * | 6/1992 | Dow, Jr. | ................. | 604/304 |
| 5,209,251 A * | 5/1993 | Curtis et al. | ........... | 132/321 |
| 5,261,169 A * | 11/1993 | Williford | ................. | 36/43 |
| 5,308,611 A | 5/1994 | Thompson | ........... | 424/78.07 |
| 5,335,373 A * | 8/1994 | Dresdner et al. | ........... | 2/161.7 |
| 5,362,754 A | 11/1994 | Raad et al. | ........... | 514/566 |
| 5,616,119 A | 4/1997 | Davis | ................. | 604/19 |
| 5,624,704 A | 4/1997 | Darouiche et al. | ........... | 427/2.24 |
| 5,709,672 A | 1/1998 | Illner | ................. | 604/265 |
| 5,756,145 A | 5/1998 | Darouiche | ........... | 427/2.24 |
| 5,811,471 A | 9/1998 | Shanbrom | ........... | 521/141 |
| 5,820,607 A | 10/1998 | Tcholakiran et al. | ........... | 604/265 |
| 5,820,918 A | 10/1998 | Ronan et al. | ........... | 427/2.1 |
| 5,853,745 A | 12/1998 | Darouiche | ........... | 424/423 |
| 5,902,283 A | 5/1999 | Darouiche et al. | ........... | 604/265 |
| 5,928,916 A | 7/1999 | Keogh | ................. | 435/174 |
| 5,965,276 A * | 10/1999 | Shlenker et al. | ........... | 428/492 |
| 6,123,926 A * | 9/2000 | Parikh et al. | ........... | 424/52 |
| 6,162,487 A | 12/2000 | Darouiche | ........... | 427/2.14 |
| 6,165,484 A | 12/2000 | Raad et al. | ........... | 424/405 |
| 6,193,994 B1 | 2/2001 | Lee et al. | ........... | 424/444 |
| 6,267,979 B1 | 7/2001 | Raad et al. | ........... | 424/405 |
| 6,284,245 B1 * | 9/2001 | Edge | ........... | 424/93.7 |
| 6,294,186 B1 * | 9/2001 | Beerse et al. | ........... | 424/405 |
| 6,344,218 B1 * | 2/2002 | Dodd et al. | ........... | 424/605 |
| 6,465,521 B1 * | 10/2002 | Rosenberg | ........... | 514/642 |
| 6,562,363 B1 * | 5/2003 | Mantelle et al. | ........... | 424/434 |
| 2002/0009693 A1 * | 1/2002 | Pelerin | ........... | 433/224 |
| 2004/0018241 A1 * | 1/2004 | Houze et al. | ........... | 424/486 |
| 2004/0132699 A1 * | 7/2004 | Zhuang et al. | ........... | 514/170 |
| 2004/0137067 A1 * | 7/2004 | Narang et al. | ........... | 424/486 |
| 2004/0165956 A1 * | 8/2004 | Greenberg | ........... | 405/128.75 |
| 2005/0049306 A1 * | 3/2005 | Harper et al. | ........... | 514/546 |

FOREIGN PATENT DOCUMENTS

| | | |
|---|---|---|
| EP | 0300961 | 1/1989 |
| EP | 0865785 | 9/1998 |
| EP | 1044686 | 10/2000 |
| GB | 2007096 | 5/1979 |
| WO | WO 00/65915 | 11/1990 |
| WO | WO 02/082907 | 10/2002 |

OTHER PUBLICATIONS

Kirk-Othmer Encyclopedia of Chemical Technology, 3rd Edition, vol. 5, pp. 857-884.*
Bhatnager and Sundaram, "Studies on antibacterial properties of gentian violet impregnated silastic," Indian J. Med. Res., [A]97:206-208, 1993.
Gonzalez et al., "Risk factors for fungemia in children infected with human immunodeficiency virus: a case control study," Clin. Infect. Dis., 23:515-521, 1996.
Lecciones et al., "Vascular catheter-associated fungemia in patients with cancer: analysis of 155 episodes," Clin. Infect. Dis., 14:875-883, 1992.
Platt and Bucknall, "MIC tests are not suitable for assessing antiseptic handwashes," J. Hosp. Infect., 11:396-397, 1988.
Raad and Bodey, "Infectious complications of indwelling vascular catheters," Clin. Infect. Dis., 15:197-210, 1992.
Raad et al., "Central venous catheters coated with minocycline and rifampin for the prevention of catheter-related colonization and bloodstream infections: a randomized, double-blind trial," Ann. Intern. Med., 127(4):267-274, 1997.

(Continued)

Primary Examiner—Elizabeth L McKane
(74) Attorney, Agent, or Firm—Fulbright & Jaworski LLP

(57) ABSTRACT

The present invention provides novel broad spectrum antiseptic compounds that further have properties that allow them to be coated/impregnated into polymer surfaces. Methods for coating these antiseptic compounds onto medical devices especially in-dwelling medical devices to prevent the growth of pathogens in such devices and hence, to prevent infection to patients via such devices are provided. The invention also provides antiseptics that are useful as general surface disinfectants and sterilizers, fluid disinfectants and biocide preservatives.

48 Claims, No Drawings

OTHER PUBLICATIONS

Raad, "Intravascular-catheter-related infections," *Lancet*, 351:893-898, 1998.

Solomon and Sherertz, "Antibiotic releasing polymers," *Controlled Release*, 6:343-352, 1987.

Tacconelli et al., "Central venous catheter-related sepsis in a cohort of 366 hospitalized patients," *Eur. J. Clin. Microbiol. Infect. Dis.*, 16:203-209, 1997.

Tumbarello et al., "Nosocomial bloodstream infections in HIV-infected patients: attributable mortality and extension of hospital stay," *J. Acquir. Immun. Defic. Syndr. Hum. Retrovirol.*, 19:490-497, 1998.

Van Delden and Iglewski, "Cell-to-cell signaling and *Pseudomonas aeruginosa* infections," *Emerging Infectious Disease*, 4(4):551-560, 1998.

Wey et al., "Risk factors for hospital-acquired candidemia," *Arch. Intern. Med.* 149:2349-2353, 1989.

Bahna et al., "Antiseptic effect of a novel alcohol-free mouthwash: a convenient prophylactic alternative for high-risk patients," *Oral Oncol.*, 43:159-164, 2007.

Heinzel, "The phenomena of resistance to disinfectants and preservatives," In *Industrial biocides*, Payne (ed.), pp. 52, 56-58, and 64-66, 1988.

Lehmann, "Synergisms in disinfectant formulations," In *Industrial biocides*, Payne (ed.), pp. 78-79 and 89, 1988.

\* cited by examiner

ANTISEPTIC DERIVATIVES WITH BROAD SPECTRUM ANTIMICROBIAL ACTIVITY FOR THE IMPREGNATION OF SURFACES

The present invention claims priority to U.S. Provisional Application Ser. No. 60/261,447 filed on Jan. 12, 2001 and U.S. Provisional Application Ser. No. 60/316,165 filed on Aug. 30, 2001, which are incorporated by reference in their entirety.

BACKGROUND OF THE INVENTION

1. Field of the Invention

The present invention relates generally to the fields of preventing infections. More particularly it provides novel broad spectrum antiseptic compositions that further have properties that allow them to be coated/impregnated into polymer surfaces or used as antiseptics in different applications. The invention provides methods for coating these antiseptic compositions onto medical devices such as catheters, tubes, stents and sutures, to prevent the growth of pathogens in such devices and hence, to prevent infection to patients via such devices. In addition, the invention provides novel antiseptics that could be used in disinfecting and sterilizing organic and inorganic surfaces, water and other fluids.

2. Description of Related Art

Most nosocomial infections are caused by the contamination of medical devices resulting in serious hospital-acquired infections. Nosocomial pneumonias are the second most common nosocomial infections, and are associated with the highest attributable mortality and morbidity. Recent data have shown that at least 300,000 episodes of nosocomial pneumonia occur annually in the United States (Official Statement, American Thoracic Society). The attributable mortality of this infection is 33%-50%, hence, around 100,000 patients die annually because of nosocomial pneumonia (CDC, 1993; Leu et al., 1989). The risk of nosocomial pneumonia increases 6- to 20-fold from the use of mechanical ventilation (Official Statement, American Thoracic Society).

The endotracheal tube is considered a common vehicle for colonization/contamination leading to nosocomial pneumonia. The endotracheal tube connects the oropharyngeal environment with the sterile bronchoalveolar space, significantly increasing the risk of nosocomial pneumonia. Endotracheal tubes are typically constructed of polyvinylchloride, which is known to be very difficult to impregnate with antiseptic or antimicrobial agents. Thus, there are no endotracheal tubes that are impregnated with antibiotics or antiseptics currently in use.

Another leading cause of serious nosocomial infections is bloodstream infections. The primary contributors to nosocomial bloodstream infections are vascular catheters. It is estimated that around 400,000 vascular catheter-related bloodstream infections (CRBSI) occur annually in the United States (Raad, 1998). The attributable mortality of these infections in the intensive care unit (ICU) was estimated in JAMA in 1994 to be 25% (Reiselman et al., 1994). Hence, these infections are a major cause of morbidity and mortality in hospitalized patients. These catheters are mostly polyurethane short-term catheters used in the ICU and long-term silicone catheters used in cancer/AIDS patients.

The most frequent causes of nosocomial infections are urinary tract infections (UTI), contributing to 34% of all nosocomial infections (Klempner et al., 1998). Nosocomial UTI are usually associated with contamination of urinary catheters. In addition, nosocomial surgical wound infections are common complications of surgical procedures, particularly in cancer and immunocompromised patients with devitalized tissue and decreased immunity. Surgical wound infections contribute to 17% of all nosocomial infections (Platt and Bucknall, 1988). Many surgical wound infections are associated with the contamination of sutures.

Antibiotics are strictly antibacterial agents that are usually used in treatment of systemic or bloodstream infections and are given through oral, intravenous, subcutaneous, or intramuscular routes to achieve systemic bloodstream levels. Examples include penicillin, cephalosporins, vancomycin, minocycline, and rifampin.

Antiseptics on the other hand, are antimicrobial agents often with broad spectrum antimicrobial activity against bacteria, fungi or viurses. These agents are used on the skin and external mucosal surfaces usually because of limitations related to absorption, penetration or systemic toxicity. These agents are not used in the treatment of bloodstream infections. Examples include chlorhexidine and povidone iodine.

Antibiotics and antiseptics have been used to impregnate vascular catheters. The concern with the use of antibiotics has been that resistance might develop to antibiotics, preventing their use therapeutically and systemically in hospitalized patients. Furthermore, the durability of the existing antiseptics has been limited. For example, the use of chlorhexidine/silver sulfadiazine on polyurethane surfaces has had limited effectiveness. Moreover, chlorhexidine/silver sulfadiazine impregnating the surface of vascular catheters resulted in limited activity against gram-negative bacilli, such as *Pseudomonas*.

What is needed is an effective antiseptic having broad spectrum activity against resistant staphylococci, vancomycin-resistant enterococci, resistant *Pseudomonas aeruginosa* and *Candida* species, to be used in conjunction with indwelling devices that will inhibit or prevent the nosocomial infections typically associated with the use of these indwelling devices. It would be further desirable to develop devices impregnated with the antiseptic to enhance the resistance to infection. For example, the creation of antiseptic-impregnated catheters would prevent organisms from adhering or migrating on catheter surfaces.

SUMMARY OF THE INVENTION

The present invention overcomes these and other drawbacks inherent in the art by providing novel antiseptic derivatives with broad-spectrum activity against various microbes including resistant bacteria and fungi. Methods of preparing these antiseptic compounds and methods for utilizing them are provided.

Therefore, the invention provides an antiseptic composition comprising a basic reagent and a dye. The basic reagent may be bonded to the dye. In one aspect, the basic reagent and the dye are bonded ionically to form the antiseptic compound. In another aspect, the basic reagent and the dye are bonded covalently to form the antiseptic compound. The basic reagent and the dye can be combined in any amount to obtain the antiseptic composition of the invention, however, in a particular embodiment, an equimolar amount of the basic reagent is added to the dye solution. The inventors also contemplate that the antiseptic composition of the invention can be made by combining other amounts of the dye and basic reagent for example, one may combine, in molar ratios, 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, to 1:99 of either dye:basic reagent or basic reagent:dye. This includes all the intermediate ranges as well, for example it includes molar ratios such as, 1.1:1, 1.2:1, 1.3:1, 1.4:1, 1.5:1, 1.6:1, 1.7:1, 1.8:1, 1.9:1 and the like for other values listed. It also includes the ranges in between these values such as 1.11:1, 1.12:1 and so on. The skilled artisan will therefore recognize that the dye and basic reagent can be combined in different molar ratio amounts to obtain the antiseptic composition disclosed and that the invention is therefore not limited to any particular molar ratio of dye:basic reagent or basic reagent:dye.

In certain embodiments, the dye can be a triarylmethane dye, a monoazo dye, a diazo dye, an indigoid dye, a xanthene or a fluorescein dye, an anthraquinone dye, or a quinoline dye. In other specific embodiments, the dye is gentian violet, or crystal violet, ethyl violet, brilliant green, an FD&C dye, or a D&C dye. In one example, the FD&C dye is Blue No. 1 or Green No. 3. In another example, the triarylmethane dye is gentian violet. In yet another example, the monoazo dye is FD&C Yellow No. 5 or FD&C Yellow No. 6. In still another example, the diazo dye is D&C Red No. 17. The indigoid dye, may preferably be FD&C Blue No. 2. An example of a xanthene dye is FD&C Red No. 3, of an anthraquinone dye is D&C Green No. 6 And an example of a quinoline dye is D&C Yellow No. 1. In addition, Table 1 provides a list of different dyes that may be used in this invention. One of skill in the art will recognize that these examples are non-limiting and that the antiseptic compounds and compositions of the present invention can be made using almost any dye.

A wide variety of basic reagents can be used to form the antiseptic composition. The basic reagents include any nucleophilic species which includes all electron donor species. Some of the basic reagents that can be used include a guanidium compound, a biguanide, a bipyridine, a phenoxide antiseptic, an alkyl oxide, an aryl oxide, a thiol, an aliphatic amine, or an aromatic amine and halides such as $F^-$, $Br^-$ and $I^-$. Some examples of guanidium compounds that may be used include chlorhexidine, alexidine, and hexamidine. One example of a bipyridine compound that can be used to synthesize the antiseptics of the invention is octenidine. Examples of phenoxide antiseptics used include colofoctol, chloroxylenol, and triclosan.

The invention also provides an antiseptic compound comprising a basic reagent bound to a dye. In some particular embodiments, the basic reagent and the dye are bound ionically. In other particular embodiments, the basic reagent and the dye are bound covalently. Some examples of the invention, the antiseptic compound comprises compositions such as gendine, genlenol, genlosan, or genfoctol.

In some embodiments, the antiseptic compound provided herein is further capable of impregnating and/or coating a surface.

In some aspects, the surface is composed of a polymer. Examples of such polymeric surfaces include polyvinyl chloride, polyurethane, polyethylene, silastic elastomers, polytetrafluoroethylene, dacron, collodion, carboethane or nylon. Alternatively, the surface may be composed of silicone or may be a silk suture. For example, these novel antiseptic derivatives have the potential for serving as impregnators of medical device surfaces, such as endotracheal tubes made of polyvinyl chloride, vascular catheters made of either polyurethane or silicone, and silk sutures used for suturing surgical wounds.

In other embodiments, the antiseptic compound can coat and/or impregnate an organic surface. Examples of organic surfaces include the skin, a mucosal surface, a wound. Examples of wounds are surgical wounds, trauma wounds, burn wounds and the like.

In yet other embodiments, the antiseptic compound can coat and/or impregnate an inorganic surface. Examples of such inorganic surfaces include floors, table-tops, countertops, surfaces of a hospital equipment, wheelchair surfaces, etc. Virtually any surface comprising a material that is capable of being coated by, impregnated with, absorbing or otherwise retaining the antiseptic compounds of the invention may be disinfected and/or sterilized using the present antiseptic compounds and their compositions. Thus, the antiseptic compound of the invention can be used to disinfect, sanitize and sterilize a wide variety of surfaces.

The invention also provides medical devices coated with a basic reagent and a dye. In one aspect the medical devices are coated with a basic reagent and a dye that are ionically bound. In another aspect the medical devices are coated with a basic reagent and a dye that are covalently bound. Examples of medical devices include endotracheal tubes, a vascular catheter, an urinary catheter, a nephrostomy tube, a biliary stent, a peritoneal catheter, an epidural catheter, a central nervous system catheter, an orthopedic device, a prosthetic valve, and a medical implant. The vascular catheter may be a central venous catheter, an arterial line, an pulmonary artery catheter, and a peripheral venous catheter. The central nervous system catheter may be an intraventricular shunt. Other medical devices that can benefit from the present invention include blood exchanging devices, vascular access ports, cardiovascular catheters, extracorpeal circuits, stents, implantable prostheses, vascular grafts, pumps, heart valves, and cardiovascular sutures, to name a few. Regardless of detailed embodiments, applicability of the invention should not be considered limited with respect to the type of medical device, implant location or materials of construction of the device.

The invention also provides methods for coating a medical device with an antiseptic compositions comprising: a) immersing a medical device in a solvent comprising a basic reagent and a dye; b) drying the device; and c) washing off excessive composition. In some embodiments, the solvent used to immerse the device can be methylene chloride, methanol, or a combination thereof.

The invention also provides methods for preventing nosocomial infections in a subject comprising coating a medical device that the subject is required to use with a composition comprising an antiseptic compound comprising a basic reagent bound to a dye. The subject can be human or an animal model.

The type of nosocomial infection that can be prevented by the methods of this invention include, but are not limited to, pneumonia, bacteremia, fungimia, candidemia, a urinary tract infection, a catheter-exit site infection, and a surgical wound infection.

The nosocomial infections that can be prevented may be caused by bacteria. In some embodiments the bacteria are drug resistant bacteria. Some non-limiting example of drug resistant bacteria include methicillin-resistant staphylococci, vancomycin-resistant enterococci, and resistant *Pseudomonas aeruginosa*.

The nosocomial infection may be caused by a fungus. In some cases the fungal agent is a drug resistant fungi. Examples of a drug resistant fungi include members of the *Candida* species. Other pathogenic organisms that can cause the nosocomial infections are cited elsewhere in this specification and coating devices and surfaces with the antiseptics of the present invention can prevent infections by these organisms as well.

The invention also provides methods for disinfecting and/or sterilizing a surface comprising applying the antiseptic composition of the invention to the surface. Examples of surfaces that may be disinfected and/or sterilized include organic surfaces such as skin, mucosal surfaces, wound surfaces and the like. Other examples include inorganic surfaces such as floors, table-tops, counter-tops, hospital equipment, wheel chairs, gauze, cotton. The skilled artisan will realize that most any surfaces can be disinfected or sterilized by the antiseptic compositions provided herein.

The invention also provides methods for disinfecting and/or sterilizing a fluid comprising adding a composition comprising a basic reagent and a dye into the fluid. The inventors contemplate that different types of fluids may be disinfected and some non-limiting examples include water, such as water in coolers and swimming pools, metal working fluids, and petroleum.

The invention also provides several novel biocide preservative compounds comprising the antiseptic compositions described above. Also provided are methods for preserving substances by applying the compositions of the invention on the substance. A variety of substances may be preserved by the biocide preservatives of the invention and they include wood, paint, plastic and paper.

Thus, the antiseptic compositions of the present invention have broad uses including use in healthcare by providing sterile medical devices and surface sterilization and decontamination, as environmental decontaminants, fluid decontaminents and in the industrial world as biocide preservatives.

As used herein the specification and claim(s), the words "a" or "an" when used in conjunction with the word "comprising" may mean one or more.

As used herein the specification and claim(s), the words "ionic bonding" or "ionically bound" refers to the electrostatic interactions among ions which can be formed by the transfer of one or more electrons from one atom or group of atoms to another, to create an ionic bond between the basic reagent and the dye comprising an antiseptic compound.

As used herein the specification and claim(s), the words "covalent bonding" or "covalently bound" refers to the chemical bond formed by the sharing of one or more pairs of electrons between the basic reagent and the dye comprising an antiseptic compound.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

A. The Present Invention

Indwelling catheters and other similar implanted medical devices are used routinely in hospitals on a diverse group of patients. A common cause of failure of these medical devices is infection. Pathogens often attach to and proliferate in such devices and eventually invade the patient leading to nosocomial infections. Microorganisms usually migrate along the surfaces of devices to invade sterile environments, such as the bronchoalveolar space leading to pneumonia, the bloodstream leading to bacteremia, or the urinary bladder leading to urinary tract infections.

The present invention provides a series of novel antiseptic compositions with broad-spectrum activity against various nosocomial microorganisms, including resistant bacteria and fungi. For example, the antiseptic compositions are effective against resistant staphylococci, vancomycin-resistant enterococci, resistant *Pseudomonas aeruginosa* and *Candida* species. These novel antiseptics also have unique properties that enable penetration/impregnation of various polymers, such as polyvinyl chloride, polyethylene, silastic elastomers, polytetrafluoroethylene, dacron, collodion, carboethane, nylon, polymers used in the formation of endotracheal tubes, silicone and polyurethane polymers used in the formation of vascular catheters and surgical silk sutures. Thus, they are suitable for coating a wide range of device surfaces.

The inventors demonstrate herein that these novel antiseptics maintain prolonged antimicrobial activity on device surfaces, and thus may be used for the entire lifespan of these indwelling devices. This is an improvement over existing coated or impregnated devices where the antimicrobial activity of the device diminishes over time and eventually disappears altogether. For example, several prior art patents and publications describe methods of coating which generated medical devices wherein the effectiveness of the coating diminishes over time. After insertion of the medical device, the antibiotics and/or antiseptics quickly leach from the surface of the device into the surrounding environment. Over a relatively short period of time, the amount of antibiotics and/or antiseptics present on the surface decreases to a point where the protection against bacterial and fungal organisms is no longer effective. Thus, the present invention provides safe antiseptic treated devices wherein the antiseptic coating has a durability that may last through the life-span of the device. This significantly decreases patient mortality and morbidity associated with the various nosocomial infections such as nosocomial pneumonias, nosocomial bacteremias, nosocomial urinary tract infections and nosocomial surgical wound infections. For example, creation of antiseptic-impregnated/coated catheters prevents organisms from adhering to or migrating on catheter surfaces. Thus, when a pathogenic organism approaches the catheter surface, it is killed by the antiseptics.

The invention also provides methods for the synthesis of novel broad-spectrum antiseptic derivatives. The general method for synthesis of the novel antiseptic derivatives involves the binding of a dye with one or more basic reagents. Different types of dyes and basic reagents can be used to prepare the antiseptic compounds of this invention.

The dyes that may be used to synthesize the antiseptic compounds of the invention include but are not limited to, gentian, or crystal violet, ethyl violet, brilliant green, etc., and the FD&C dyes such as Blue No. 1 and Green No. 3. In addition, other dyes include the following FD&C and D&C colors: (1) Monoazo dyes such as, but not limited to, FD&C Yellow No. 5, FD&C Yellow No. 6, (2) Diazo dyes such as, but not limited to, D&C Red No. 17, (3) Indigoid dyes such as, but not limited to, FD&C Blue No. 2, (4) Xanthene (Fluorescein) dyes such as, but not limited to, FD&C Red No. 3, (5) Anthraquinone dyes such as, but not limited to, D&C Green No. 6, (6) Quinoline dyes such as, but not limited to, D&C Yellow No. 1. An extensive list of dyes and stains that may be employed is also provided in Table 1.

The basic reagents can be alkyl and aryl oxides, thiols, sulfides, phosphorous, aliphatic and aromatic amines, guanidines and halides such as $F^-$, $Br^-$ and $I^-$. Some examples of the basic reagents that can be used include phenoxide antiseptics (such as clofoctol, chloroxylenol, triclosan) or guanidium compounds (such as chlorhexidine, alexidine, hexamidine) or bipyridines (such as octenidines).

TABLE 1

The Color Index (C.I.) Number and/or Chemical Abstracts Service Registry CAS) Number for Dyes and Stains that may be Employed to Stain Medical Devices:

| No. | C.I. # | CAS # |
|---|---|---|
| 1 | 15670 | 2092-55-9 |
| 2 | 26370 | 3071-73-6 |
| 3 | 20460 | 5850-35-1 |
| 4 | 62130 | 2666-17-3 |
| 5 | 61585 | 4474-24-2 |
| 6 | 26360 | 3351-05-1 |
| 7 | 62058 | 6397-02-0 |
| 8 | 42685 | 3244-88-0 |
| 9 | 61580 | 6408-57-7 |
| 10 | 15575 | 5850-86-2 |
| 11 | 22870 | 15792-50-4 |
| 12 | 18050 | 3734-67-6 |
| 13 | 14900 | 4787-93-3 |
| 14 | 18070 | 12167-45-2 |
| 15 | 22890 | 10169-02-5 |
| 16 | 23635 | 6459-94-5 |
| 17 | 18800 | 6408-31-7 |
| 18 | 18055 | 4321-69-1 |
| 19 | 18965 | 6359-98-4 |
| 20 | 18900 | 6359-91-7 |
| 21 | 25135 | 13390-47-1 |
| 22 | 22910 | 6375-5-9 |
| 23 | 18850 | 6359-88-2 |
| 24 | 46005:1 | 494-38-2 |
| 25 | | 8048-52-0 |
| 26 | 58000 | 72-48-0 |
| 27 | | 3952-78-1 |
| 28 | 61710 | 6408-63-5 |
| 29 | 42750 | 30586-13-1 |
| 30 | | 569-58-4 |
| 31 | | 52417-22-8 |
| 32 | | 520-10-5 |
| 33 | 48035 | 3056-93-7 |
| 34 | | 4431-00-9 |
| 35 | 50090 | 25360-72-9 |
| 36 | 52010 | 531-55-5 |
| 37 | 61111 | 12217-43-5 |
| 38 | 42500 | 569-61-9 |
| 39 | 11460 | 42373-04-6 |
| 40 | 23500 | 992-59-6 |
| 41 | | 298-95-3 |
| 42 | 21010 | 5421-66-9 |
| 43 | | 1871-22-3 |
| 44 | 28440 | 2519-30-4 |
| 45 | 42660 | 6104-59-2 |
| 46 | 27290 | 5413-75-2 |
| 47 | 24890 | 3051-11-4 |
| 48 | | 76-60-8 |
| 49 | | 115-40-2 |
| 50 | | 115-39-9 |
| 51 | 65005 | 1328-24-1 |
| 52 | 62055 | 6408-78-2 |
| 53 | 62125 | 6424-85-7 |
| 54 | 63010 | 2861-02-1 |
| 55 | 13390 | 3861-73-2 |
| 56 | 26400 | 3529-01-9 |
| 57 | 15706 | 12392-64-2 |
| 58 | 61570 | 4403-90-1 |
| 59 | 62560 | 4430-16-4 |
| 60 | 26550 | 8003-88-1 |
| 61 | 18745 | 10127-27-2 |
| 62 | 14710 | 5858-39-9 |
| 63 | 17045 | 6360-07-2 |
| 64 | 15620 | 1658-56-6 |
| 65 | 18110 | 6844-74-2 |
| 66 | 26900 | 6406-56-0 |
| 67 | 18125 | 10130-48-0 |
| 68 | 42650 | 4129-84-4 |
| 69 | 18835 | 6359-85-9 |
| 70 | 18890 | 6359-90-6 |
| 71 | 18950 | 6372-96-9 |
| 72 | 14170 | 6408-90-8 |
| 73 | 13900 | 10343-58-5 |
| 74 | 46025 | 135-49-9 |
| 75 | 12840 | 61968-76-1 |
| 76 | 63615 | 1324-21-6 |
| 77 | 58005 | 130-22-3 |
| 78 | 14025 | 584-42-9 |
| 79 | 42080 | 3486-30-4 |
| 80 | 16185 | 915-67-3 |
| 81 | 42780 | |
| 82 | | 1668-00-4 |
| 83 | 41000 | 2465-27-2 |
| 84 | 43810 | 13186-45-3 |
| 85 | 52005 | 531-53-3 |
| 86 | 51004 | 33203-82-6 |
| 87 | 11075 | 94233-04-2 |
| 88 | 42510 | 632-99-5 |
| 89 | 48055 | 4208-80-4 |
| 90 | 26905 | 4196-99-0 |
| 91 | | 2315-97-1 |
| 92 | 21000 | 10114-58-6 |
| 93 | 16180 | 5858-33-3 |
| 94 | 42655 | 6104-58-1 |
| 95 | | 81029-05-2 |
| 96 | 42040 | 633-03-4 |
| 97 | | 102185-52-4 |
| 98 | | 62625-32-5 |
| 99 | | 62625-30-3 |
| 100 | | 62625-28-9 |
| 101 | | 14337-53-2 |
| 102 | | 76-59-5 |
| 103 | | 40070-59-5 |
| 104 | | 3147-14-6 |
| 105 | 24410 | 2610-05-1 |
| 106 | 43825 | 1667-99-8 |
| 107 | 16575 | 548-80-1 |
| 108 | 43820 | 3564-18-9 |
| 109 | 24895 | 2870-32-8 |
| 110 | 18972 | 50662-99-2 |
| 111 | | 596-27-0 |
| 112 | | 2303-01-7 |
| 113 | | 1733-12-6 |
| 114 | | 10510-54-0 |
| 115 | 15970 | 1934-20-9 |
| 116 | | 15391-59-0 |
| 117 | | 76-54-0 |
| 118 | | 4727-50-8 |
| 119 | | 54-88-6 |
| 120 | | 6473-13-8 |
| 121 | 23655 | 6420-03-7 |
| 122 | 25380 | 2829-43-8 |
| 123 | 27905 | 5489-77-0 |
| 124 | 13950 | 10190-68-8 |
| 125 | 29025 | 3214-47-9 |
| 126 | 64500 | 2475-45-8 |
| 127 | 61500 | 2475-44-7 |
| 128 | 1005 | 730-40-5 |
| 129 | | 31482-56-1 |
| 130 | 11115 | 3180-81-2 |
| 131 | 11855 | 2832-40-8 |
| 132 | 26090 | 6300-37-4 |
| 133 | 45400 | 548-24-3 |
| 134 | 45380 | 548-26-5 |
| 135 | | 15086-94-9 |
| 136 | 14640 | 3564-14-5 |
| 137 | 42090 | 3844-45-9 |
| 138 | 45430:2 | 15905-32-5 |
| 139 | 45386 | 6359-05-3 |
| 140 | | 76058-33-8 |
| 141 | 23860 | 314-13-6 |
| 142 | 11160 | 97-56-3 |
| 143 | 13015 | 2706-28-7 |
| 144 | 11285 | 6416-57-5 |
| 145 | 45350:1 | 2321-07-5 |
| 146 | | 596-09-8 |

TABLE 1-continued

The Color Index (C.I.) Number and/or Chemical Abstracts Service Registry CAS) Number for Dyes and Stains that may be Employed to Stain Medical Devices:

| No. | C.I. # | CAS # |
|---|---|---|
| 147 |  | 3326-34-9 |
| 148 | 51030 | 1562-85-2 |
| 149 |  | 1634-82-8 |
| 150 |  | 3737-95-9 |
| 151 |  | 165660-27-5 |
| 152 |  | 16574-43-9 |
| 153 |  | 34722-90-2 |
| 154 |  | 617-19-6 |
| 155 | 51050 | 1562-90-9 |
| 156 |  | 4430-20-0 |
| 157 | 14720 | 3567-69-9 |
| 158 | 16570 | 4197-07-3 |
| 159 | 11270 | 532-82-1 |
| 160 | 18105 | 17681-50-4 |
| 161 | 22120 | 573-58-0 |
| 162 |  | 2411-89-4 |
| 163 |  | 62625-31-4 |
| 164 |  | 62625-29-0 |
| 165 |  | 41830-80-2 |
| 166 | 42555 | 548-62-9 |
| 167 | 45370:1 | 596-03-2 |
| 168 |  | 620-45-1 |
| 169 | 45425:1 | 31395-16-1 |
| 170 |  | 73688-85-4 |
| 171 | 34140 | 4399-55-7 |
| 172 | 29160 | 3441-14-3 |
| 173 | 28160 | 2610-11-9 |
| 174 | 13920 | 10130-29-7 |
| 175 | 19556 | 6537-66-2 |
| 176 | 36900 | 6409-90-1 |
| 177 | 61505 | 2475-46-9 |
| 178 | 11080 | 2581-69-3 |
| 179 | 26080 | 6253-10-7 |
| 180 | 11110 | 2872-52-8 |
| 181 | 11130 | 2734-52-3 |
| 182 | 12790 | 6439-53-8 |
| 183 |  | 518-82-1 |
| 184 |  | 56360-46-4 |
| 185 | 45380:2 | 15086-94-9 |
| 186 | 14645 | 1787-61-7 |
| 187 | 18760 | 3618-63-1 |
| 188 | 45430 | 568-63-8 |
| 189 |  | 1239-45-8 |
| 190 |  | 62758-12-7 |
| 191 | 42600 | 2390-59-2 |
| 192 | 37190 | 64071-86-9 |
| 193 | 42053 | 2353-45-9 |
| 194 | 12010 | 6535-42-8 |
| 195 | 18820 | 6359-82-6 |
| 196 | 45350 | 518-47-8 |
| 197 |  | 3326-32-7 |
| 198 |  | 51649-83-3 |
| 199 | 42085 | 4680-78-8 |
| 200 | 75290 | 517-28-2 |
| 201 |  | 90-33-5 |
| 202 | 73000 | 482-89-3 |
| 203 | 73015 | 860-22-0 |
| 204 | 12210 | 4569-88-4 |
| 205 | 11050 | 2869-83-2 |
| 206 | 44090 | 3087-16-9 |
| 207 | 42000 | 2437-29-8 |
| 208 | 13065 | 587-98-4 |
| 209 | 52041 | 2516-05-4 |
| 210 | 45385 | 23391-49-3 |
| 211 | 13025 | 547-58-0 |
| 212 |  | 32469-43-5 |
| 213 | 14855 | 3624-68-8 |
| 214 | 11335 | 6247-27-4 |
| 215 | 11880 | 6370-46-3 |
| 216 | 11300 | 6232-53-7 |
| 217 | 26520 | 3564-27-0 |
| 218 | 18735 | 1934-24-3 |
| 219 | 14010 | 6054-99-5 |
| 220 | 44530 | 5715-76-4 |
| 221 | 11350 | 131-22-6 |
| 222 | 16255 | 2611-82-7 |
| 223 | 52030 | 6586-05-6 |
| 224 |  | 7385-67-3 |
| 225 |  | 74-39-5 |
| 226 | 60760 | 6409-77-4 |
| 227 | 26120 | 4477-79-6 |
| 228 | 16230 | 1936-15-8 |
| 229 | 15705 | 2538-85-4 |
| 230 | 19010 | 10127-05-6 |
| 231 | 42045 | 129-17-9 |
| 232 |  | 34487-61-1 |
| 233 |  | 101-75-7 |
| 234 | 11800 | 1689-82-3 |
| 235 | 45410 | 18472-87-2 |
| 236 | 16680 | 1058-92-0 |
| 237 | 27190 | 6226-78-4 |
| 238 | 49000 | 30113-37-2 |
| 239 |  | 16593-81-0 |
| 240 |  | 85531-30-2 |
| 241 | 45005 | 92-32-0 |
| 242 | 58500 | 81-61-8 |
| 243 | 47000 | 8003-22-3 |
| 244 | 20505 | 17095-24-8 |
| 245 | 61205 | 13324-20-4 |
| 246 | 17908 | 25489-36-5 |
| 247 |  | 635-78-9 |
| 248 | 45170 | 81-88-9 |
| 249 | 45160 | 989-38-8 |
| 250 | 45440 | 632-69-9 |
| 251 | 50240 | 477-73-6 |
| 252 | 61552 | 6994-46-3 |
| 253 |  | 7423-31-6 |
| 254 |  | 3599-32-4 |
| 255 |  | 146-68-9 |
| 256 | 42095 | 5141-20-8 |
| 257 | 42000:1 | 510-13-4 |
| 258 |  | 129-16-8 |
| 259 | 52015 | 61-73-4 |
| 260 | 50206 | 4569-86-2 |
| 261 | 42590 | 7114-03-6 |
| 262 | 13020 | 493-52-7 |
| 263 | 11020 | 60-11-7 |
| 264 | 20110 | 3564-15-6 |
| 265 | 11875 | 6247-28-5 |
| 266 | 13250 | 3618-62-0 |
| 267 | 14030 | 2243-76-7 |
| 268 | 26560 | 6406-37-7 |
| 269 |  | 6408-91-9 |
| 270 | 14045 | 6470-98-0 |
| 271 | 20470 | 1064-48-8 |
| 272 | 50040 | 553-24-2 |
| 273 | 42520 | 3248-91-7 |
| 274 | 51180 | 3625-57-8 |
| 275 | 14890 | 5423-07-4 |
| 276 |  | 56431-61-9 |
| 277 | 61555 | 2646-15-3 |
| 278 | 26125 | 1320-06-5 |
| 279 | 15510 | 633-96-5 |
| 280 | 15711 | 5610-64-0 |
| 281 | 12070 | 6410-10-2 |
| 282 |  | 143-74-8 |
| 283 | 11000 | 60-09-3 |
| 284 |  | 16201-96-0 |
| 285 |  | 975-17-7 |
| 286 |  | 2768-90-3 |
| 287 | 27195 | 6226-79-5 |
| 288 |  | 67627-18-3 |
| 289 | 58205 (75410) | 81-54-9 |
| 290 |  | 115-41-3 |
| 291 | 45010 | 2150-48-3 |
| 292 |  | 117-92-0 |

TABLE 1-continued

The Color Index (C.I.) Number and/or Chemical Abstracts Service Registry CAS) Number for Dyes and Stains that may be Employed to Stain Medical Devices:

| No. | C.I. # | CAS # |
| --- | --- | --- |
| 293 | 58050 | 81-64-1 |
| 294 | 47005 | 8004-92-0 |
| 295 | 61211 | 12236-82-7 |
| 296 | 17757 | 12225-82-1 |
| 297 | 61200 | 2580-78-1 |
| 298 | | 123333-76-6 |
| 299 | 45170:1 | 509-34-2 |
| 300 | | 13161-28-9 |
| 301 | 43800 | 603-45-2 |
| 302 | 61554 | 17354-14-2 |
| 303 | 61565 | 128-80-3 |
| 304 | 12055 | 842-07-9 |
| 305 | 12140 | 3118-97-6 |
| 306 | 26105 | 85-83-6 |
| 307 | 11920 | 2051-85-6 |
| 308 | | 123359-42-2 |
| 309 | | 23647-14-5 |
| 310 | 45100 | 3520-42-1 |
| 311 | 19140 | 1934-21-0 |
| 312 | | 108321-10-4 |
| 313 | | 62637-91-6 |
| 314 | | 6262-21-1 |
| 315 | | 632-73-5 |
| 316 | | 42798-98-1 |
| 317 | 19540 | 1829-00-1 |
| 318 | 52000 | 78338-22-4 |
| 319 | | 81012-93-3 |
| 320 | | 123359-43-3 |
| 321 | 12120 | 2425-85-6 |
| 322 | 23850 | 72-57-1 |
| 323 | 44045 | 2580-56-5 |
| 324 | 42595 | 2390-60-5 |
| 325 | | 125-31-5 |
| 326 | 16150 | 3761-53-3 |
| 327 | | 135-52-4 |
| 328 | 26100 | 85-86-9 |
| 329 | 26150 | 4197-25-5 |
| 330 | 26050 | 6368-72-5 |
| 331 | | 68504-35-8 |
| 332 | | 123333-78-8 |
| 333 | 45220 | 5873-16-5 |
| 334 | | 4430-25-5 |
| 335 | | 1301-20-8 |
| 336 | | 123333-63-1 |
| 337 | | 386-17-4 |
| 338 | | 4430-24-4 |
| 339 | | 1719-71-7 |
| 340 | 49005 | 2390-54-7 |
| 341 | | 76-61-9 |
| 342 | | 125-20-2 |
| 343 | 52040 | 92-31-9 |
| 344 | 14270 | 547-57-9 |
| 345 | | 14541-90-3 |
| 346 | 44040 | 2185-86-6 |
| 347 | 45190 | 6252-76-2 |
| 348 | | 63721-83-5 |
| 349 | | 14936-97-1 |

One unique feature of these novel antiseptics is that they do not require another vehicle to attach to a surface. The adhesive potential of the dye makes them self-adhesive to surfaces of devices.

The antiseptic compound is therefore applied on the surface of a device by simply immersing the device in the antiseptic solution, air drying and washing out excessive antiseptic. The self-impregnating property of the dyes such as for example, the triarylmethane dyes, removes the need for another binding agent. This is another feature of the composition provided by this invention which is a considerable improvement over other known compositions. Previously known compositions require other impregnating/coating agents and/or must typically be extruded into the device as it is made. Both these methods are time consuming and involve additional steps and techniques. For example, one method of coating devices first requires application or absorption of a layer of surfactant, such as tridodecylmethyl ammonium chloride (TDMAC) followed by the antibiotic coating layer, to the surface of the medical device. Another method used to coat surfaces of medical devices with antibiotics involves first coating the selected surfaces with benzalkonium chloride followed by ionic bonding of the antibiotic composition (Solomon and Sherertz, 1987; U.S. Pat. No. 4,442,133). Other methods of coating surfaces of medical devices with antibiotics are taught in U.S. Pat. No. 4,895,566 (a medical device substrate carrying a negatively charged group having a pH of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders). Furthermore, most of the methods previously employed to coat the surfaces of medical devices use antibiotics such as tetracyclines, penicillins, cephalosporins and the beta-lactam antibiotics. The main drawback with antibiotics is the emergence of resistant strains.

Thus, the invention provides novel antiseptic derivative compounds with broad-spectrum antiseptic activity against bacteria and fungi including nosocomial and multidrug-resistant varieties with the additional ability to impregnate, bind, coat, adhere and/or attach to various device surfaces without the assistance of impregnating vehicles such as tridodecylmethylammonium chloride (TDMAC). Furthermore, the novel antiseptic compounds of the invention also have an extended antimicrobial efficacy that can cover the life of the device.

One example of the novel broad-spectrum antiseptic derivatives of this invention is gendine, which consists of the combination of gentian violet and chlorhexidine. Gentian violet, on its own, is a good impregnating triarylmethane dye. Bhatnager et al., 1993 have shown in an in vitro study that gentian violet alone can be used to impregnate the surface of CSF silicone shunts and prevent the colonization of *S. epidermis* on these surfaces. However, after impregnating the surfaces of various polymers, including polyvinylchloride, gentian violet on its own has no activity against *Pseudomonas aeruginosa*, which is the second most common cause of nosocomial pneumonia and the third most common cause of nosocomial urinary tract infections. Antiseptics such as chlorhexidine cannot attach on their own onto the surfaces of polyvinylchloride tubes or silicone catheters and silk sutures. They require an impregnating vehicle. Furthermore, on their own they are not highly active against *Pseudomonas aeruginosa*. On the other hand, upon the binding of gentian violet with chlorhexidine, the new antiseptic agent synthesized, is a potent and effective broad-spectrum antiseptic and has the additional ability to coat/impregnate various device surfaces. Gendine is unique in its ability to impregnate various device polymers, such as polyvinylchloride used in the formation of endotracheal tubes, silicone and polyurethane polymers used in the formation of vascular, as well as peritoneal, epidural, urinary and intraventricular catheters. In addition, gendine is able to impregnate the silk sutures used in surgical wounds.

In addition to Gendine, other antiseptics encompassed by this invention are Genlenol and Genfoctol.

The invention also provides methods to generate a wide variety of antiseptic medical devices. Some examples include antiseptic endotracheal tubes, antiseptic vascular catheters, including central venous catheters, arterial lines, pulmonary artery catheters, and peripheral venous catheters, antiseptic urinary catheters, antiseptic nephrostomy tubes, antiseptic biliary stents, antiseptic peritoneal catheters, antiseptic epidural catheters, antiseptic central nervous system catheters, including intraventricular shuts and devices, antiseptic prosthetic valves, orthopedic implants and antiseptic sutures.

B. Pathogens

The nosocomial bacterial infections result in diseases such as bacteremia, pneumonia, meningitis, osteomyelitis, endocarditis, sinusitis, arthritis, urinary tract infections, tetanus, gangrene, colitis, acute gastroenteritis, bronchitis, and a variety of abscesses, and opportunistic infections. Bacterial pathogens include Gram-positive cocci such as *Staphylococcus aureus*, coagulase negative staphylocci such as *Staphylococcus epidermis, Streptococcus pyogenes* (group A), *Streptococcus* spp. (viridans group), *Streptococcus agalactiae* (group B), *S. bovis, Streptococcus* (anaerobic species), *Streptococcus pneumoniae*, and *Enterococcus* spp.; Gram-negative cocci such as *Neisseria gonorrhoeae, Neisseria meningitidis*, and *Branhamella catarrhalis*; Gram-positive bacilli such as Bacillus anthracis, *Corynebacterium diphtheriae* and Corynebacterium species which are diptheroids (aerobic and anerobic), *Listeria monocytogenes, Clostridium tetani, Clostridium difficile, Escherichia coli, Enterobacter* species, *Proteus mirablis* and other spp., *Pseudomonas aeruginosa, Klebsiella pneumoniae, Salmonella, Shigella, Serratia*, and *Campylobacter jejuni*. The antibiotic resistant bacteria that can be killed by the antiseptic coated devices of the present invention include *Staphylococci* (methicillin-resistant strains), vancomycin-resistant enterococci (*Enterococcus faecium*), and resistant *Pseudomonas aeruginosa*.

Fungal infections that may be prevented include fungal infections (mycoses), which may be cutaneous, subcutaneous, or systemic. Superficial mycoses include tinea capitis, tinea corporis, tinea pedis, onychomycosis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis (phycomycosis), paracoccidioidomycosis, North American blastomycosis, histoplasmosis, coccidioidomycosis, and sporotrichosis. Fungal infections include opportunistic fungal infections, particularly in immunocompromised patients such as those with AIDS. Fungal infections contribute to meningitis and pulmonary or respiratory tract diseases. Other pathogenic organisms that may be prevented from causing the infections include dermatophytes (*Microsporum canis* and other M spp.; and *Trichophyton* spp. such as *T. rubrum*, and *T. mentagrophytes*), yeasts (e.g., *Candida albicans, C. Parapsilosis, C. glabrata, C. Tropicalis*, or other *Candida* species including drug resistant *Candida* species), *Torulopsis glabrata, Epidermophytonfloccosum, Malassezia fuurfur* (*Pityropsporon orbiculare*, or *P. ovale*), *Cryptococcus neoformans, Aspergillus fumigatus*, and other *Aspergillus* spp., *Zygomycetes* (*Rhizopus, Mucor*), hyalohyphomycosis (*Fusarium* Spp.), *Paracoccidioides brasiliensis, Blastomyces dermatitides, Histoplasma capsulatum, Coccidioides immitis*, and *Sporothrix schenckii*. Fungal infections include *Cladosporium cucumerinum, Epidermophyton floccosum*, and *Microspermum ypseum*.

C. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Gendine and Impregnation of Devices

Impregnation Procedure

The general procedure involves, and when applicable, prior preparation of the basic reagent (such as chlorhexidine) in anhydrous solvent, addition of the basic reagent to a solution of a dye (such as Gentian violet) in anhydrous solvent (or addition of the dye to the basic solution), stirring the resulting mixture for 30-90 minutes at ambient conditions, evaporating the solvent also under ambient conditions, and finally dissolution of the residue prior to impregnation. The following procedure illustrates impregnation with Gendine, an example for employing a basic guanidium derivative (e.g., chlorhexidine) and triarylmethane dye (e.g., Gentian violet).

Potassium tert-butoxide in THF, 7.35 ml of 1M solution, was added to a solution of CHX diacetate, 1.533 g; 2.45 mmol in 35 ml THF. The resulting heterogeneous solution was stirred for 20 minutes, then added to a solution GV, 1.0 g; 2.45 mmol, in 30 ml THF (GV used as an example of Triarylmethane Dye). The mixture was stirred at ambient conditions for 1 hour, then placed under the hood overnight to evaporate the solvent. The resulting residue was dissolved in 30 ml DCM (or MeOH). When applicable, the base (such as neutral form of chlorhexidine) is added to a stirring solution of dye (such as GV) in DCM and the resulting mixture is stirred for at least 1 h. With anionic dyes, dissolution is achieved with the addition of at least one equivalent of a quaternary amine (such as tetraethylammonium) prior to addition of the base. One-centimeter device segments were immersed in the DCM solution for the appropriate period, generally PVC and PU for 10 minutes; Silicone (Si) and Silk Suture for 2 hours. The devices were removed from the solution, and traces of solution were removed from the lumen when applicable. The impregnated devices were placed under the hood to dry for at least 4 hours, preferably over night, then washed with distilled water until the washings were colorless or very faint, and finally placed under an aseptic hood to dry under ambient conditions for at least 4 hours, preferably overnight.

In Vitro Antimicrobial Activity

The antimicrobial activity of impregnated catheters was evaluated in duplicate by a modified Kirby-Bauer technique. BBL Mueller Hinton II agar plates (obtained from Fisher Scientific) were inoculated with 0.5 McFarland of the appropriate microorganism (hospital isolates from the MD Anderson Cancer Center). Then 10 mm segments of impregnated devices were embedded in the inoculated plates and placed in an incubator at about 37° C. for at least 18 hours. Zones of inhibition were measured perpendicular to the long axis of the device. Bioactivity against yeast constituted of two zones; a large outer zone of partial growth inhibition, and an inner smaller zone of complete inhibition. This later zone is reported herein.

Results and Discussion

Tables 2 and 3 illustrate zones of inhibition obtained for Gendine-impregnated devices:

TABLE 2

Endotracheal PVC Tubes, (7.0 mm I.D.)

| Reagent in DCM | Zones of Inhibition (in mm) obtained for | | |
|---|---|---|---|
| | MRSA$_{2066}$ | PS$_{4205}$ | C. Parap.$_{1\text{-}100\text{-}0022}$ |
| GV[†] | 25:25 | 0:0 | 27:27 |
| CHX[††, §] | 0:0 | 0:0 | 0:0 |
| GN, 1$^{st}$ trial[†] | 28:28 | 21:21 | 27:28 |
| GN, 2$^{nd}$ trial[‡] | 28:29 | 22:23 | 27:27 |

MRSA = Methicillin-Resistant *Staphylococcus aureus*.
PS = *Pseudomonas aeruginosa*
C. Parap. = *Candida Parapsilosis*
[§]DCM solution containing about 33% MeOH$_{v/v}$.
[†]Device immersed for 10 minutes.
[††]Device immersed for 2 hours.
[‡]Device immersed for 1 hour.

TABLE 3

Endotracheal PVC Tubes, (7.0 mm I.D.)

| Reagent in MeOH | Zones of Inhibition (in mm) obtained for | | |
|---|---|---|---|
| | MRSA$_{2066}$ | PS$_{4205}$ | C. Parap.$_{1\text{-}100\text{-}0022}$ |
| GV[†] | 20:21 | 0:0 | 18:19 |
| CHX[†] | 0:0 | 0:0 | 0:0 |
| GN[†] | 24:25 | 13:13 | 23:23 |

[†]Device immersed for 2 hours.

As shown in Tables 2 and 3, endotracheal PVC tubes impregnated with Gendine (GN) are far more effective against all organisms when compared with those impregnated with CHX, and more effective than PVC tubes impregnated with GV against *Pseudomonas aeruginosa*.

TABLE 4

Double lumen 10.0 FR-Cook Silicone Catheter

| Reagent in DCM | Zones of Inhibition (in mm) obtained for | | |
|---|---|---|---|
| | MRSA$_{2066}$ | PS$_{4205}$ | C. Parap.$_{1\text{-}100\text{-}0022}$ |
| GV[†] | 6:7 | 0:0 | 0:0 |
| CHX[†, §] | 0:0 | 0:0 | 0:0 |
| GN, 1$^{st}$ trial[†] | 18:19 | 11:12 | 19:19 |
| GN, 2$^{nd}$ trial[‡] | 19:19 (19:20)[‡] | 10:11 (12:13)[‡] | 18:18 (24:25)[‡] |

MRSA = Methicillin-Resistant *Staphylococcus aureus*.
PS = *Pseudomonas aeruginosa*
C. Parap. = *Candida Parapsilosis*
[§]DCM solution containing about 33% MeOH$_{v/v}$.
[†]Device immersed for 2 hours.
[‡]Values between parenthesis are for 20 hour immersions.

Again data in Table 4 shows how silicone catheters impregnated with GN are more effective in inhibiting MRSA, PS and C. parapsilosis than catheters impregnated with either GV or CHX.

TABLE 5

Double lumen 10.0 FR-Polyurethane Catheter

| Reagent in DCM | Zones of Inhibition (in mm) obtained for | | |
|---|---|---|---|
| | MRSA$_{2066}$ | PS$_{4205}$ | C. Parap.$_{1\text{-}100\text{-}0022}$ |
| GV[†] | 22:22 | 0:0 | 22:23 |
| CHX[††, §] | 17:17 | 10:10 | 15:15 |
| GN, 1$^{st}$ trial[†] | 21:21 | 13:14 | 26:27 |
| GN, 2$^{nd}$ trial[‡] | 22:22 | 15:15 | 22:23 |

MRSA = Methicillin-Resistant *Staphylococcus aureus*.
PS = *Pseudomonas aeruginosa*
C. Parap. = *Candida Parapsilosis*
[†]Device immersed for 10 minutes.
[††]Device immersed for 2 hours.
[§]DCM solution containing about 33% MeOH$_{v/v}$.
[‡]Device immersed for 1 hour.

Similarly, Table 5 indicates that PU catheters impregnated with GN are more effective than PU catheter impregnated with GV in inhibiting *Pseudomonas aeruginosa*, and more effective than PU catheters impregnated with CHX against all three organisms, MRSA, PS and C. parapsilosis.

TABLE 6

Silk Sutures

| Reagent | Zones of Inhibition (in mm) obtained for | | |
|---|---|---|---|
| | MRSA$_{2066}$ | PS$_{4205}$ | C. Parap.$_{1\text{-}100\text{-}0022}$ |
| GV[†] | 8:8 | 0:0 | 0:0 |
| CHX[†, §] | 0:0 | 0:0 | 0:0 |
| GN, 1$^{st}$ trial[†] | 17:17 | 3:5 | 21:21 |
| GN, 2$^{nd}$ trial[†] | 15:15 | 4:4 | 14:14 |

MRSA = Methicillin-Resistant *Staphylococcus aureus*.
PS = *Pseudomonas aeruginosa*
C. Parap. = *Candida Parapsilosis*
[†]Device immersed for 2 hours.
[§]DCM solution containing about 33% MeOH$_{v/v}$.

Table 6 as well shows that silk sutures coated or impregnated with GN are significantly more effective in inhibiting MRSA, PS and C. parapsilosis than sutures coated with either GV or CHX.

In addition to the simplicity of the impregnation procedure, and the availability of the requisite reagents, one unique feature of gendine-impregnated devices is its broad spectrum activity, not only against the worldwide problematic gram-positive MRSA, which has increased in frequency at an alarming rate as a cause of device-related infections, but also against *Pseudomonas aeruginosa*, an increasingly prevalent opportunistic human pathogen, and the most common gram-negative bacterium found in nosocomial infections. They are intrinsically more resistant than gram-positive bacteria to many antiseptics, particularly when present in a biofilm or when associated with a device infection (Platt et al., 1988).

For PVC and silicone (Si) devices, this invention shows no activity against *Pseudomonas aeruginosa*, when impregnated with either the immobilizing dye (gentian violet) or CHX alone. All devices impregnated with GN exhibit fair to good activity against *Pseudomonas aeruginosa*. This is important especially since *Pseudomonas aeruginosa* is responsible for 16% of nosocomial pneumonia cases (and is considered by the Centers for Disease Control as the second most common cause of nosocomial ventilator associated pneumonia), 12% of nosocomial urinary tract infections, 8% of surgical wound infections, and 10% of nosocomial bloodstream infections (Van Delden and Iglewski, 1998).

Staphylococcal resistance to antiseptics are known worldwide (Russel A. D., 1997). In addition to CHX, low-level resistance to three antiseptics (acriflavin, benzalkonium chloride, and hexamidine diisethionate is documented (Reverdy et al., 1992; Townsend et al., 1985; Heir et al., 1995). The present study reveals that all GN-impregnated devices, including sutures, exhibit significant biocidal activity against methicillin-resistant staphylococci. This finding is extremely important in light of the fact that methicillin-resistant staphylococci (MRSA and MRSE) are the leading causes of device-related infections, including vascular catheter-related bacteremia and surgical wound infections. In addition S. aureus is one of the leading causes of nosocomial pneumonia (Klempner et al., 1998).

The effectiveness of gendine-impregnated devices against Candida is no less noteworthy. As revealed from this study, silicone catheter and suture impregnated with GN exhibit fair to good activity against C. Parapsilosis, which is not the case for either GV or CHX-impregnated devices. Catheter-related candidemia is now the third leading cause of vascular catheter-related bloodstream infections (Raad et al., 1992). In addition, candidemia in severely immunocompromised patients (i.e., HIV, bone-marrow recipients and leukemia patients) is an important cause for morbidity and mortality and catheters are a major source for this infection (Tumbarello et al., 1998; Gonzalez et al., 1996; Lecciones et al., 1992; Wey et al., 1989). The known chlorhexidine-sulfadiazine impregnated catheters and the minocycline-rifampin impregnated catheters do not have significant prophylactic effect against fungi (Tacconelli et al., 1997; Raad et al., 1997).

Other GV Preparations

Antiseptics chloroxylenol [p-chloro-m-xylenol; 4-chloro-3,5-dimethylxylenol (PCMX)], Clofoctol [α-2,4-dichlorophenly)-4-(1,1,3,3-tetramethylbutyl)-o-cresol (CFTL), and Triclosan [2,4,4'-trichloro-2'hydroxydiphenyl ether] (TLS) are three of the phenolic antiseptic reagents included in this study. The first disinfectant is the first halophenol employed in many antiseptic and disinfectant formulations. Neither the neutral form of PCMX nor its sodium salt could produce in vitro zones of inhibition on their own through coating or impregnating the catheter devices and sutures. However, when the salt is reacted with GV (as an example of a triarylmethane dye), the resulting products (new products such as Genlenol, Genlosan and Genfoctol) are immobilized on the devices producing large in vitro zones of inhibition against various nosocomial pathogens. Meanwhile, Genlenol (GV$^+$.PCMX$^-$) not only increased the zone against MRSA considerably for the silicone catheter, but also produced a large zone against C. parapsilosis. Similar results were observed for silk sutures. Improvements in the zones of inhibition against C. parapsilosis are also observed for PVC tubes and PVC catheters, and to a large extent against Alcaligenes faecalis (a gram negative bacillary organism) for the PVC tubes. These results are summarized in Tables 7-10. Similar trends were observed for Genfoctol (GV$^+$.CFTL$^-$), but with much larger zones for sutures against MRSA and C. parapsilosis.

TABLE 7

Zones of Inhibition (in mm) imparted by endotracheal$^f$ PVC tubes

| | Zones of Inhibition (in mm) against | | |
|---|---|---|---|
| Reagent | MRSA$_{2066}$ | Alcaligenes faecalis$_{3681}$ | C. Parap.$_{1\text{-}100\text{-}0022}$ |
| GV$^\dagger$ | 25:25 | 18:18 | 27:27 |
| PCMX | 0:0 | 0:0 | 0:0 |
| GV$^+$.PCMX$^{-*}$ | 27:27 | 27:28 | 34:34 |

$^f$7.0 mm I.D.
$^\dagger$Gentian violet.
$^\ddagger$Chloroxylenol.
*Genlenol.

TABLE 8

Zones of Inhibition (in mm) imparted by Silicone catheters$^f$

| | Zones of Inhibition (in mm) against | | |
|---|---|---|---|
| Reagent | MRSA$_{2066}$ | Alcaligenes faecalis$_{3681}$ | C. Parap.$_{1\text{-}100\text{-}0022}$ |
| GV$^\dagger$ | 6:7 | 0:0 | 0:0 |
| PCMX$^\ddagger$ | 0:0 | 0:0 | 0:0 |
| GV$^+$.PCMX$^{-*}$ | 16:16 | 0:0 | 16:16 |
| CFTL$^\S$ | 0:0 | 0:0 | 0:0 |
| GV$^+$.CFTL$^{-\mathit{II}}$ | 20:20 | 10:10 | 28:29 |

$^f$Double lumen 10.0 FR-Cook Silicone catheter.
$^\dagger$Gentian violet.
$^\ddagger$Chloroxylenol.
*Genlenol.
$^\S$Clofoctol.
$^{\mathit{II}}$Genfoctol.

TABLE 9

Zones of Inhibition (in mm) imparted by Polyurethane catheters$^f$

| | Zones of Inhibition (in mm) against | | |
|---|---|---|---|
| Reagent | MRSA$_{2066}$ | Alcaligenes faecalis$_{3681}$ | C. Parap.$_{1\text{-}100\text{-}0022}$ |
| GV$^\dagger$ | 22:22 | 18:18 | 22:23 |
| PCMX$^\ddagger$ | 0:0 | 0:0 | 0:0 |
| GV$^+$.PCMX$^{-*}$ | 24:24 | 18:20 | 31:31 |
| CFTL$^\S$ | 0:0 | 0:0 | 0:0 |
| GV$^+$.CFTL$^{-\mathit{II}}$ | 23:23 | 15:17 | 30:32 |

$^f$Double lumen 10.0 FR-catheter.
$^\dagger$Gentian violet.
$^\ddagger$Chloroxylenol.
*Genlenol.
$^\S$Clofoctol.
$^{\mathit{II}}$Genfoctol.

TABLE 10

Zones of Inhibition Imparted by Silk Sutures

| | Zones of Inhibition (in mm) against | |
|---|---|---|
| Reagent | MRSA$_{2066}$ | C. Parap.$_{1\text{-}100\text{-}0022}$ |
| GV$^\dagger$ | 8:8 | 0:0 |
| PCMX$^\ddagger$ | 0:0 | 0:0 |
| GV$^+$.PCMX$^{-*}$ | 11:11 | 5:5 |

TABLE 10-continued

Zones of Inhibition Imparted by Silk Sutures

| | Zones of Inhibition (in mm) against | |
|---|---|---|
| Reagent | MRSA$_{2066}$ | C. Parap.$_{1\text{-}100\text{-}0022}$ |
| CFTL$^\S$ | 0:0 | 0:0 |
| GV$^+$.CFTL$^{\mathit{II}}$ | 17:17 | 15:16 |

$^\dagger$Gentian violet.
$^\ddagger$Chloroxylenol.
*Genlenol.
$^\S$Clofoctol.
$^{\mathit{II}}$Genfoctol.

In general, many other gentian violet basic preparations significantly affect the efficacy and biocidal activity of coated sutures and silicone-impregnated catheters against MRSA and *C Parapsilosis*. Some examples are shown below in Table 11.

TABLE 11

Zones of Inhibition Imparted by Silicone Catheters and Silk Sutures

| | Zones of Inhibition (in mm) against | | | |
|---|---|---|---|---|
| | MRSA$_{2066}$ | | C. Parap.$_{1\text{-}100\text{-}0022}$ | |
| Reagent | Si-catheter | Silk Suture | Si-catheter | Silk Suture |
| GV$^\dagger$ | 6:7 | 8:8 | 0:0 | 0:0 |
| GV$^+$OH$^-$ | 18:19 | 17:17 | 19:19 | 13:14 |
| GV$^+$OCH$_3^-$ | 18:19 | 15:15 | 25:25 | 10:13 |
| GV$^+$Glycerin$^-$ | 19:20 | 13:14 | 18:18 | 9:9 |
| GV$^+$HEDTA$^{-4\ddagger}$ | 13:13 | 7:7 | 9:13 | 4:5 |
| GV$^+$TCSA$^{-\S}$ | 14:14 | 12:13 | 11:11 | 10:10 |
| GV$^+$MBT$^{-\mathit{II}}$ | 13:13 | 8:8 | 12:12 | 0:0 |

Gentian violet.
$^\ddagger$Trisodium n-(2-Hydroxyethyl)ethylenediaminetriacetate.
$^\S$TCSA = 3',4',5-Trichlorosialicyl-anilide.
$^{\mathit{II}}$MBT = 2-Mercaptobenzothiazole.

The above data clearly demonstrate significant improvement in the biocidal activity of impregnated or coated silicone catheters and silk sutures by the antiseptic derivatives of the invention.

Example 2

Clinical Trials

The antiseptic devices of the invention pose no significant risk. Hence, preclinical studies (animal studies) may not be required. This section is concerned with the development of human treatment protocols using the antiseptic medical devices of the present invention.

The various elements of conducting a clinical trial, including patient treatment and monitoring, will be known to those of skill in the art in light of the present disclosure. The following information is being presented as a general guideline for use in establishing the use of the antiseptic medical devices.

Candidates will be patients who are seriously ill and are required to use a medical device such as those described in the sections above. The medical devices in these cases will be treated with Gendine, Genelol, Genfoctol, Genlosan or other antiseptic derivatives that can be synthesized by the methods provided herein, and the patients will be monitored for the occurrence of nosocomial infections.

To monitor the development of infections and to evaluate the efficacy of the antiseptic coated/impregnated medical devices in preventing the spread of infectious agents through the devices it is contemplated that the patients will be examined for appropriate tests every month. Tests that will be used to monitor the effectiveness of the treated medical device include: physical exam, X-ray, blood work and other clinical laboratory methodologies used to detect pathogens in the patients and also methods to detect presence of pathogens in the medical device. Described below is a study guideline for patients using central venous catheters.

A. Efficacy of Central Venous Catheters Coated with Antiseptics of the Invention Patient Eligibility. Patients will be recruited from intensive care units, bone marrow transplant and melanoma services and other hospital divisions where catheters are used routinely on inpatients. Patients who require a new insertion of a central venous catheter (CVC) and have none of the exclusion criteria will be approached to obtain informed consent. The exclusion criteria are the following:

1. Age<18 years
2. Dermatitis over catheter insertion site
3. Pregnancy
4. Allergy to chlorhexidine or gentian violet
5. Expected duration of catheter placement <3 days
6. Inability to obtain informed consent The eligible consenting patient will be informed that the catheter to be inserted has either been coated with an antiseptic compound (for example Gendine) or has not been coated, but the subject will not be informed as to whether the specific catheter to be inserted contains the compound.

Each female with child bearing potential will have a urine sample prior to catheter placement to test for pregnancy (if appropriate).

Catheter Insertion. Catheters will be inserted into a subclavian vein or internal jugular vein using gown, mask, sterile gloves and full sterile drapes. Skin will be prepped using povidone iodine allowing 1 minute of exposure time. After insertion, the catheter will be secured to the skin using tape and the skin puncture site will be covered with povidone-iodine ointment. Then, the insertion site and the surrounding area will be covered with sterile gauze and taped securely.

Catheter Maintenance. Catheters will be inspected every 72 hrs for evidence of site infection (erythema around catheter, purulent drainage, swelling tenderness over catheter). Every 72 hrs (or sooner if necessary) the dressing will be removed and the exit site will be re-prepped with povidone-iodine. All fluids, medications, etc. administered through each lumen will be documented.

Catheter Types. The inventors contemplate using different types of catheters. For example, control catheters consist of triple lumen polyurethane catheters and single lumen polyurethane catheters will be tested among several others. The test catheters will be identical to the control catheters in appearance, but they will be coated with the antiseptics of the invention, for example, Gendine.

Trial Design. The trial is a prospective randomized design. The patient, the health care worker inserting the catheter, the microbiologist culturing the catheter, and the evaluator will be blinded as to whether the catheter is coated or not coated with the antiseptics of the invention. They will, however, be identifiable by an assigned code number. After informed consent has been obtained a catheter will be pulled out of a box containing 6 test and control catheter placement trays. The boxes will consist of either triple or single lumen catheters and will be labeled as such. The trays will be placed in the boxes such that test and control catheters will alternate from top to bottom. Each box will contain 3 test and 3 control catheters. The unique identification number of the catheter will be recorded and will be included with the data analysis. Both the investigators and the patients will be blinded to the catheter identity throughout the study.

Statistical Considerations. Assuming a conservative baseline colonization and/or infection rate of at least 20% for central venous catheters, randomizing 75 patients to each arm would allow one to detect a change in catheter-related infection rates from 20% to 5% one sided significance and 80% power. If, after entering 150 patients, the infection rate in the test arm has dropped by 50% (that is from 20% to 10%) then the study will be expanded to include 400 patients (200 in each arm). Using the selection criteria described above, the inventors estimate that they will test about 40 patients each month. Aiming for a total of 150 evaluable patients the study will be completed in approximately 6 months.

Termination of Study. Patients will be kept on study until the catheter is removed. The indication for catheter removal will be documented for each catheter. These include but are not limited to:
1. Catheter no longer needed
2. Catheter leaks
3. Bleeding around catheter
4. Catheter thrombosis
5. Catheter insertion site infection or sepsis
6. Positive blood cultures that are thought to be clinically significant (i.e. associated fever, increased WBC) and no other site of infection is identifiable.

When the patient becomes febrile, blood will be withdrawn simultaneously through the lumen of the catheter and peripheral vein for quantitative blood culture. At the time of catheter removal, the catheter will be removed under aseptic conditions and the tip and intracutaneous segments saved for culturing using the roll plate and sonication quantitative catheter culture technique. At the time of removal each lumen will be marked as to its prior use (hyperalimentation).

Patient Evaluation

1. Pre-Insertion Evaluation. Pertinent history will be taken and physical examination will be done regarding inclusion and exclusion criteria. Demographic data as well as details pertaining to underlying malignancy, treatment and antimicrobial treatment (including antimicrobial prophylaxis for infections in general in patients with hematologic malignancies) will be recorded. Investigational nature of study will be explained and informed consent will be obtained from patient. Pregnancy tests (serum or urine) will be obtained on all female patients with child bearing potential. If the test is positive, the patient will be excluded.

Initial catheterization procedure details will be recorded including catheter type, site and date of placement; difficulty of insertion, and complications if any. The difficulty of insertion will be determined by noting the following (a) number of attempts to insert the catheter (b) time spent during insertion (c) malpositioning and repositioning of a catheter.

2. Post-Insertion Evaluation. All patients will be monitored until the catheter is removed. Catheter site evaluation will be undertaken every 72 hrs with the change of dressing. Special attention will be given to erythema, infiltration, pain, tenderness, swelling, suppuration, palpable cord in vessel, tissue warmth, lymphangitis or phlebitis. Details pertaining to chemotherapy, antineoplastic and antimicrobials, will be recorded. Catheter usage as for agents that might cause sclerosis of the vessel involved, hyperalimentation, blood and blood products administration, and drawing of blood will be noted. The catheter insertion site will be recorded on every patient. In addition, events of repositioning the catheter after displacement will be recorded. Microbiologic evaluation of insertion site will be undertaken in the form of site cultures if suppuration is present. If catheter related septicemia is suspected, blood cultures will be drawn simultaneously through catheter and by peripheral venipuncture. Another set of cultures will be drawn 24 hours later. If thrombophlebitis is suspected venous flow study of involved vessel will be done. If line related infection is suspected (including in patients with fever of unknown origin) or septicemia is documented, catheter will be changed over guide wire and distal as well as the proximal 5-7 cm of the catheter will be evaluated for semiquantitative cultures by the inventors. The purpose of this procedure is diagnostic and not therapeutic. It will attempt to make a definitive diagnosis of catheter related infection by isolating the organism from the catheter using quantitative techniques.

3. End of Evaluation. When it is decided to withdraw the line, the catheter will be evaluated by the inventors for quantitative cultures. In addition, a quantitative blood culture will be drawn through the CVC lumen if the lumen is patent and peripherally if the patient is febrile.

Catheter Assessment

Definitions

1. Catheter tunnel infection: Either the proximal and/or the distal catheter segments growing >15 colonies by the roll-plate culture technique or >100 colonies by the sonication culture technique.

2. Catheter exit site infection: development of lymphangitis, purulence or two of the following: erythema, tenderness, induration or warmth.

3. Catheter related septicemia: Recovery of same organism from catheter segment and blood without any other identifiable source for the septicemia. The catheter should grow at least 15 colonies of the organism by roll plate or at least 100 colonies by sonication. The patient should have clinical manifestation of sepsis (fever, chills or sudden hypotension).

4. Catheter-related infection: any of the conditions defined above would be considered as catheter-related infection.

Success will be measured if there is no catheter related infection and failure will be indicated by the presence of a catheter related infection.

Adverse Reactions. All patients will be monitored for an unexpected adverse reaction (e.g. increased inflammation, phlebitis) associated with the coated catheter, using a statistical sequential test method. The study will be stopped if major adverse reaction is identified. Otherwise, the study will continue until 75 patients in each group have been enrolled.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

American Thoracic Society. Official Statement. Hospital-acquired pneumonia in adults: diagnosis, assessment of severity, initial antimicrobial therapy and preventative strategies. A consensus statement. *Respir. Crit. Care Med.*, 153:1711-1725, 1996.

Bhatnager, Sundaram, Studies on antibacterial properties of gentian violet impregnated silastic, *Indian J. Med. Res.*, [A]97:206-208, 1993.

Centers for Disease Control and Prevention. Morbidity and Mortality Weekly Report CDC Surveillance, 46:891, 1993.

Delden and Iglewski, Cell-to-cell signaling and *Pseudomonas aeruginosa* infections, *Emerging Infectious Diseases*, 4:551-560, 1998.

Gonzalez, Venzon, Lee, Mueller, Pizzo, Walsh, Risk factors for fungemia in children infected with human immunodeficiency virus: a case control study, *Clin. Infect. Dis.*, 23:515-521, 1996.

Heir, Sundheim, Holck, Resistance to quaternary ammonium compounds in *Staphylococcus* spp. Isolated from the food industry and nucleotide sequence fo the resistance plasmid pST827, *J. Appl. Bacteriol.*, 79:149-156, 1995.

Klempner, Lorber, Bartlett, Hospital infections and healthcare epidemiology, In: INFECTIOUS DISEASES: MEDICAL KNOWLEDGE SELF-ASSESSMENT PROGRAM, $2^{ND}$ EDITION, American College of Physicians, Philadelphia, Pa., pp. 210, 1998.

Lecciones, Lee, Navarro, Vascular catheter-associated fungemia in patients with cancer: analysis of 155 episodes, *Clin. Infect. Dis.* 14:875-883, 1992.

Leu, Kaiser, Mori, Hospital-acquired pneumonia: attributable mortality and morbidity, *Am. J. Epidemiol.*, 129:1258-1267, 1989.

Platt, Bucknall, MIC tests are not suitable for assessing antiseptic handwashes, *J. Hosp. Infect.*, 11:396-397, 1988.

Raad, Bodey, Infectious complications of indwelling vascular catheters, *Clin. Infect. Dis.* 15:197-210, 1992.

Raad, Darouiche, Dupuis, Central venous catheters coated with minocycline and rifampin for the prevention of catheter-related colonization and bloodstream infections: a randomized, double-blind trial, *Ann. Intern. Med,* 127:267-274, 1997.

Raad, Intravascular-catheter-related infections, *Lancet*, 351: 893-898, 1998.

Reiselman, Tarara, Wenzel, Nosocomial bloodstream infections in the critically ill, *JAMA,* 272:1578-1601, 1994.

Reverdy, Bes, Nervi, Martra, Fleurette, Activity of four antiseptics (acriflavin, benzalkonium chloride, chlorhexidine digluconate and hexamidine di-isethionate) and of ethidium bromide on 392 strains representing 26 *Staphylococcus* species, *Med. Microbiol. Lett.*, 1:56-63, 1992.

Russell, Plasmids and bacterial resistance to biocides, *J. App. Microbiol.*, 82:157-161, 1997.

Solomon, D. D. and Sherertz, R. J., *J. Controlled Release,* 6:343-352, 1987.

Tacconelli, Tumbarello, Pittiruti, Central venous catheter-related sepsis in a cohort of 366 hospitalized patients, *Eur. J. Clin. Microbiol. Infect. Dis.*, 16:203-209, 1997.

Townsend, Ashdown, Momoh, Grubb, Distribution of plasmid-born resistance to nucleic acid binging compounds in methicillin resistant *Staphylococcus aureus, J. Antimicrob. Chemother.* 15:417-434, 1985.

Tumbarello, Tacconelli, Donati, Nosocomial bloodstream infections in HIV-infected patients: attributable mortality and extension of hospital stay, *J. Acquir. Immun. Defic. Syndr. Hum. Retrovirol.*, 19:490-497, 1998.

U.S. Pat. No. 4,107,121
U.S. Pat. No. 4,442,133
U.S. Pat. No. 4,895,566
U.S. Pat. No. 4,917,686
U.S. Pat. No. 4,952,419
U.S. Pat. No. 5,013,306
U.S. Pat. No. 5,709,672

Wey, Mori, Pfaller, Woolson, Wenzel, Risk factors for hospital-acquired candidemia, *Arch. Intern. Med.* 149:2349-2353, 1989.

What is claimed is:

1. A method for disinfecting and/or sterilizing a floor, a table-top, a counter-top, hospital equipment, a wheel chair, or a medical device comprising applying a composition consisting essentially of chlorhexidine and a dye selected from the group consisting of gentian violet and brilliant green to the floor, table-top, counter-top, hospital equipment, wheel chair, or medical device, wherein the molar ratio of chlorhexidine:dye in the composition is 1:1 to 25:1.

2. The method of claim 1, further defined as a method for disinfecting and/or sterilizing a medical device comprised of a polymer.

3. The method of claim 2, wherein the polymer is silicone, polyvinyl chloride, polyurethane, polyethylene, silastic elastomers, polytetrafluoroethylene, dacron, collodion, carboethane or nylon.

4. The method of claim 3, wherein the medical device is comprised of silicone.

5. The method of claim 1, wherein the dye is gentian violet.

6. The method of claim 1, wherein the dye is brilliant green.

7. The method of claim 1, further defined as a method for disinfecting and/or sterilizing a medical device selected from the group consisting of an endotracheal tube, a catheter, a nephrostomy tube, a biliary stent, an orthopedic device, a prosthetic valve, a medical implant, a blood exchanging device, a vascular access port, an extracorporeal circuit, a stent, an implantable prosthesis, a vascular graft, a pump, and a heart valve.

8. The method of claim 7, wherein the medical device is a catheter.

9. The method of claim 8, wherein the catheter is a cardiovascular catheter, a vascular catheter, a urinary catheter, a peritoneal catheter, an epidural catheter, a central nervous system catheter, a pulmonary artery catheter, a peripheral venous catheter, or an intraventricular shunt.

10. The method of claim 9, wherein the dye is gentian violet.

11. The method of claim 9, wherein the dye is brilliant green.

12. The method of claim 7, wherein the medical device is an endotracheal tube.

13. The method of claim 12, wherein the dye is gentian violet.

14. The method of claim 13, wherein the dye is brilliant green.

15. The method of claim 1, wherein the ratio of chlorhexidine:dye in the composition is 5:1 to 20:1.

16. The method of claim 15, wherein the molar ratio of chlorhexidine:dye in the composition is 7:1 to 15:1.

17. The method of claim 16, wherein the molar ratio of chlorhexidine:dye in the composition is 8:1 to 10:1.

18. The method of claim 1, wherein the composition is applied to a floor.

19. The method of claim 1, wherein the composition is applied to a table-top.

20. The method of claim 1, wherein the composition is applied to a counter-top.

21. The method of claim 1, wherein the composition is applied to hospital equipment.

22. The method of claim 1, wherein the composition is applied to a wheel chair.

23. The method of claim 1, wherein the composition is applied to a medical device.

24. The method of claim 23, wherein the medical device is a catheter.

25. The method of claim 24, wherein the catheter is a cardiovascular catheter.

26. The method of claim 24, wherein the catheter is a urinary catheter.

27. The method of claim 24, wherein the catheter is a peritoneal catheter.

28. The method of claim 24, wherein the catheter is a an epidural catheter.

29. The method of claim 24, wherein the catheter is a central nervous system catheter.

30. The method of claim 24, wherein the catheter is a pulmonary artery catheter.

31. The method of claim 24, wherein the catheter is a peripheral venous catheter.

32. The method of claim 24, wherein the catheter is an intraventricular shunt.

33. The method of claim 23, wherein the medical device is an endotracheal tube.

34. The method of claim 23, wherein the medical device is a medical implant.

35. The method of claim 23, wherein the medical device is a nephrostomy tube.

36. The method of claim 23, wherein the medical device is a biliary stent.

37. The method of claim 23, wherein the medical device is an orthopedic device.

38. The method of claim 23, wherein the medical device is a prosthetic valve.

39. The method of claim 23, wherein the medical device is a blood exchanging device.

40. The method of claim 23, wherein the medical device is a vascular access port.

41. The method of claim 23, wherein the medical device is an extracorporeal circuit.

42. The method of claim 23, wherein the medical device is a stent.

43. The method of claim 23, wherein the medical device is an implantable prosthesis.

44. The method of claim 23, wherein the medical device is a vascular graft.

45. The method of claim 23, wherein the medical device is a pump.

46. The method of claim 23, wherein the medical device is a heart valve.

47. A method for disinfecting and/or sterilizing a floor, a table-top, a counter-top, hospital equipment, a wheel chair, or a medical device comprising applying a composition consisting essentially of:
   a) chlorhexidine;
   b) a dye that is gentian violet or brilliant green; and
   c) one or more additional dyes selected from the group consisting of crystal violet, FD&C Yellow No. 5, FD&C Yellow No. 6, D&C Red NO. 17, FD&C Red No. 3, D&C Green No. 6, ethyl violet, FD&C Blue No. 2, D&C Yellow No. 1, FD&C Blue No. 1, and FD&C Green No. 3 to a floor, table-top, counter-top, hospital equipment, wheel chair, or medical device, wherein the molar ratio of chlorhexidine:dye in the composition is 1:1 to 25:1.

48. A method for disinfecting and/or sterilizing a floor, a table-top, a counter-top, hospital equipment, a wheel chair, or a medical device comprising applying a composition consisting essentially of:
   a) a basic reagent that is chlorhexidine;
   b) a dye that is gentian violet or brilliant green; and
   c) one or more additional basic reagents selected from the group consisting of a guanidium, a biguanide, a bipyridine, a phenoxide antiseptic, an alkyl oxide, a thiol, a halide, an aliphatic amino, and an aromatic amine
to a floor, table-top, counter-top, hospital equipment, wheel chair, or medical device, wherein the molar ratio of chlorhexidine:dye in the composition is 1:1 to 25:1.

* * * * *